United States Patent [19]

Choksi

[11] Patent Number: 4,635,647
[45] Date of Patent: Jan. 13, 1987

[54] INCENTIVE SPIROMETER EMPLOYING BELLOWS AIR FLOW SENSOR

[76] Inventor: Pradip V. Choksi, 10935 Yolanda Ave., Northridge, Calif. 91326

[21] Appl. No.: 648,243

[22] Filed: Sep. 7, 1984

[51] Int. Cl.[4] .............................................. A61B 5/08
[52] U.S. Cl. ..................................... 128/728; 272/99; 128/725
[58] Field of Search ...................... 128/725, 727, 728; 272/99

[56] References Cited

U.S. PATENT DOCUMENTS

| | | | |
|---|---|---|---|
| 3,754,546 | 8/1973 | Cooper | 272/99 |
| 3,848,583 | 11/1974 | Parr | 128/728 |
| 4,143,872 | 3/1979 | Havstad et al. | 272/99 |
| 4,233,990 | 11/1980 | Yardley | 128/728 |
| 4,299,236 | 11/1981 | Poirier | 128/728 |
| 4,323,078 | 4/1982 | Heimlich | 128/728 |
| 4,391,283 | 7/1983 | Sharpless et al. | 128/727 |
| 4,425,805 | 1/1984 | Ogura et al. | 128/725 |
| 4,487,207 | 12/1984 | Fitz | 128/728 |
| 4,495,944 | 1/1985 | Brisson et al. | 128/725 |
| 4,546,793 | 10/1985 | Stupecky | 128/725 |

FOREIGN PATENT DOCUMENTS 0084159 7/1983 European Pat. Off. ............ 128/725

Primary Examiner—Kyle L. Howell
Assistant Examiner—Ruth S. Smith
Attorney, Agent, or Firm—Spensley Horn Jubas & Lubitz

[57] ABSTRACT

Disclosed is an incentive spirometer employing a collapsible bellows switch mechanism for determining when the rate of air flow into a patient's lungs is within a desired range. A timing circuit determines the time during which the flow rate is within the desired range and this information is displayed giving an incentive display of the air volume inhaled by the patient.

22 Claims, 4 Drawing Figures

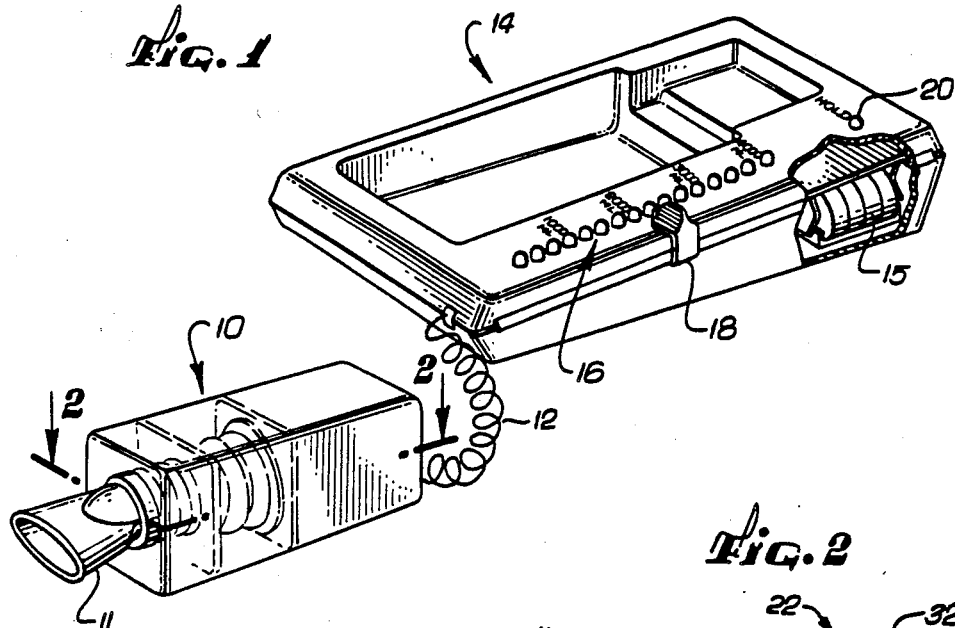
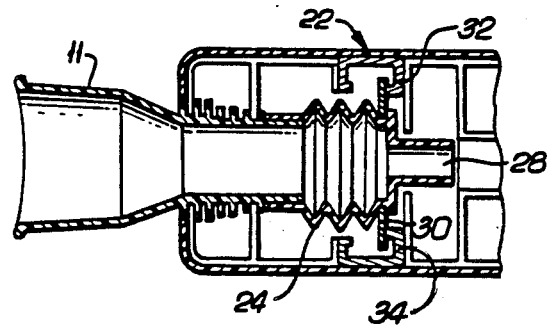
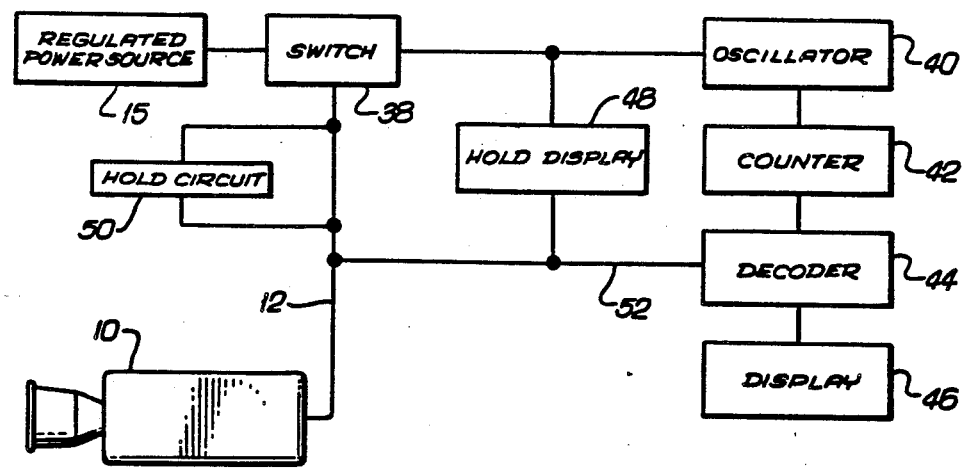

INCENTIVE SPIROMETER EMPLOYING BELLOWS AIR FLOW SENSOR

BACKGROUND OF THE INVENTION

1. Field of the Invention

This invention relates to lung exercisers for providing incentive feedback to patients engaged in remedial breathing exercises. In particular, this invention relates to lung exercisers utilizing inhaled air volume measurement and display for goal setting during breathing exercises.

2. Background of the Invention

Incentive spirometers are used by convalescing patients to measure progress and provide incentive for proper lung exercising. For example, post-operative patients who have undergone abdominal surgery can take only shallow breaths to avoid pain in the surgical site. This shallow breathing causes collapse and eventual necrosis of the lung alveoli, referred to as atelactasis. The shallow breathing also slows down the patient's recovery rate. To avoid atelactasis and to speed up recovery, the currently accepted technique is to encourage the patient to take slow deep breaths. Lung exercising devices that encourage patients to take deep breaths are known as incentive spirometers.

The prior art lung exercisers may be classified as either flow measuring or volume measuring devices. Flow measuring lung exercisers are commonly inexpensive, toy-like devices. For example, a simple flow measuring lung exerciser may comprise a mouthpiece and tube attached to a larger tube with a lightweight ball inside. Suction on the mouthpiece creates a partial vacuum which causes the ball to rise, thereby giving a rough indication of the air flow rate through the tube. Such air flow measuring lung exercisers suffer from the disadvantage of only encouraging rapid inhalation whereas the desired breathing procedure is taking slow deep breaths. Furthermore, such inexpensive flow measuring lung exercisers are of questionable incentive due to the crude feedback provided and due to their toy-like appearance. In particular, for younger children a more sophisticated, electronic incentive display is desired.

Prior art volume measuring incentive spirometers currently in use are expensive, relatively bulky devices. As a result, this type of spirometer is normally taken from patient to patient by a therapist as the cost is prohibitive to each patient having their own incentive spirometer. One type of such spirometer in common use measures volume by counting the number of revolutions of a turbine placed in a disposable air flow tube through which the patient inhales. The accuracy of this device depends upon the friction in the bearings and the inertia of the turbine. The reusable part of the unit employs a microcomputer to analyze the information from the turbine and provide a feedback display to the patient. Although the feedback provided is reasonably accurate, the overall device is bulky and expensive. Also, the device permits stacking of breaths. The patient can take several short breaths before the turbine stops spinning. This would show up as one deep breath.

SUMMARY OF THE INVENTION

Accordingly, it is an object of the present invention to provide a relatively inexpensive incentive spirometer capable of providing an incentive display encouraging slow, deep breathing.

It is a further objective to provide an incentive spirometer where "stacking of breaths" is not possible.

It is a further object of the present invention to provide an incentive spirometer having an electronic and visually effective display of inhaled air volume for patient goal setting.

It is yet another object of the present invention to provide an incentive spirometer of compact size and weight capable of being easily carried about by a convalescing patient.

The above and other objects are accomplished in the present invention by providing an incentive spirometer employing an air flow sensor to determine when the air flow rate during inhalation falls within a predetermined relatively narrow range corresponding to desired slow breathing. The air flow sensor employs a flexible bellows having a calculated collapse characteristic to measure the air flow rate therethrough. The bellows forms part of a switch mechanism which activates a timing circuit and display system while the air flow rate is within the predetermined range. The timing circuit employs a counter to count periodic pulses and provide an output related thereto to sequentially light an LED display thereby providing the patient a visually effective readout of the total air volume inhaled and providing incentive for slow, deep breathing. A hold circuit and a hold display are also provided as an incentive to the patient to hold the air in his lungs for a desired period of time.

DESCRIPTION OF THE DRAWINGS

FIG. 1 is a perspective view of a preferred embodiment of the incentive spirometer.

FIG. 2 is a cross-section view of the hand-held air flow sensor.

FIG. 3 is a block diagram showing the operation of the incentive spirometer.

DESCRIPTION OF THE PREFERRED EMBODIMENT

Figure 4:
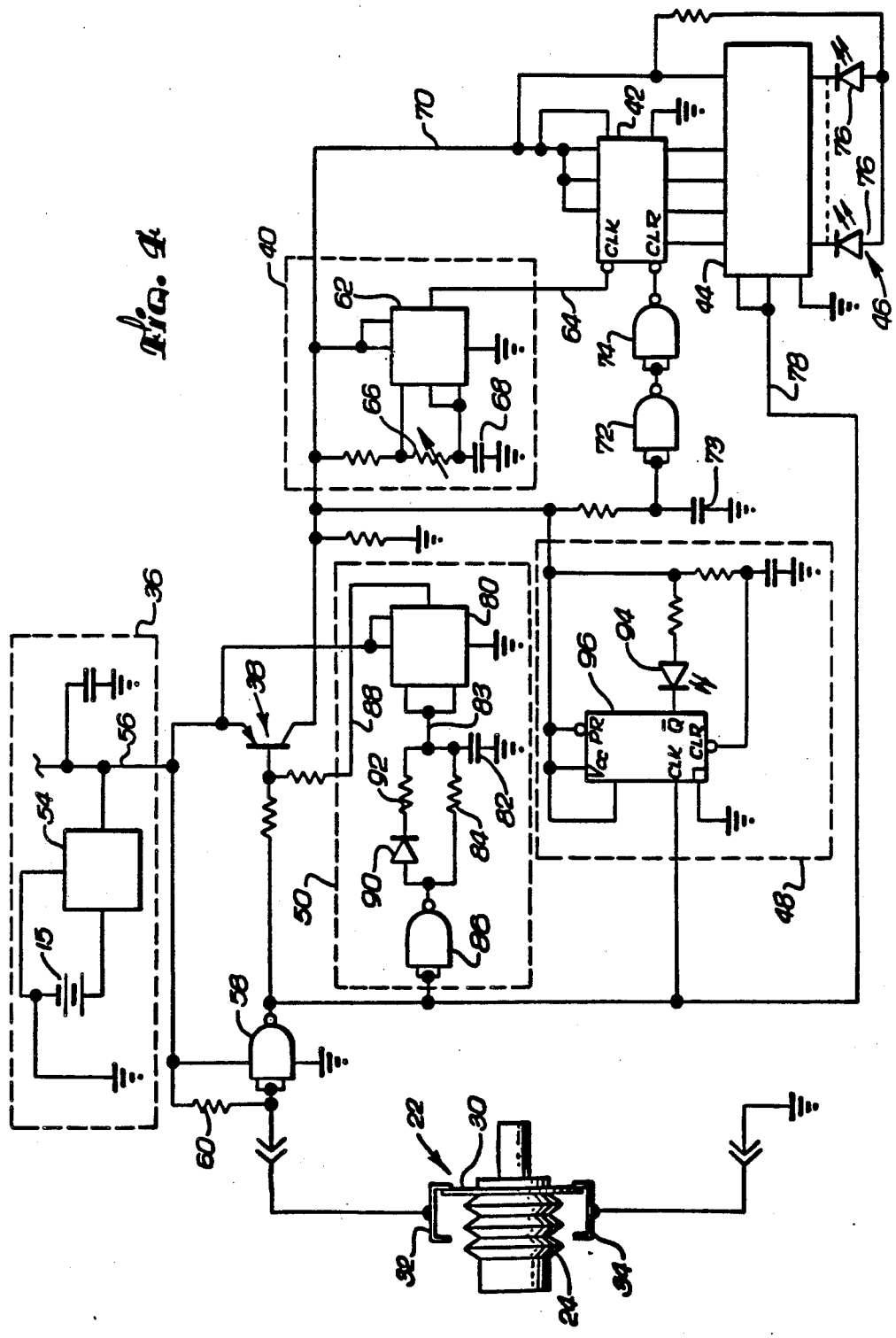
FIG. 4 is a schematic diagram showing a preferred embodiment of the circuitry of the incentive spirometer.

In FIG. 1 a preferred embodiment of the incentive spirometer is shown. In the embodiment shown the spirometer has an aesthetically pleasing shape and a compact size suitable for convalescing patients to keep at their bedside in a hospital or take home with them. The spirometer employs a hand-held air flow sensor 10 having a mouthpiece 11. During breathing exercises, the patient inhales through mouthoiece 11 and the air flow sensor 10 determines when the air flow rate falls within a predetermined range corresponding to desired slow breathing. The air flow sensor 10 is connected by a long flexible electrical connecting cord 12 to the base unit 14 which contains the spirometer electronics and incentive displav. The spirometer electronics activates the incentive display while the air flow rate is within the desired range, varying the display with time to indicate inhaled air volume. The spirometer electronics and incentive display are powered by a standard D.C. battery 15.

The incentive display may take the form of a series of light emitting diodes (LEDs) 16 which sequentially light up to display the volume of air inhaled. A sliding marker 18 is provided as a goal setting incentive for the patient. A hold display is also provided, in the form of an additional LED 20, to encourage the patient to hold the air in his lungs while the hold display is on. The spirometer's electronics allows considerable flexibility for the form of incentive display and other forms of visual, or even audible, feedback may be provided. In this regard, it has been found that electronic-based incentive displays, such as the LEDs 16 shown in FIG. 1, provide a greater incentive for the patient than simple toy-like mechanical displays. In addition, the LED display 16 shown in FIG. 1 allows easily visible feedback in even a dimly lit room.

In FIG. 2 the air flow sensor 10 is shown in cross-section. The air flow sensor 10 employs a simple but effective switch mechanism 22 designed to encourage slow deep breathing by the patient and allow a relatively accurate measurement of inhaled air volume. The switch mechanism 22 employs a collapsible bellows 24 which is attached to the mouthpiece 11 of the air flow sensor 10. As the patient inhales through the mouthpiece 11 the air flows through the orifice 28 and bellows 24, creating a force proportional to the air flow rate tending to collapse the bellows 24. The relation between the air flow rate and the collapsing force on the bellows 24 is approximately linear and thus the extent of collapse of the bellows 24 provides a measurement of the air flow rate.

The bellows switch mechanism 22 employs an electrically conductive metal annulus 30 attached to one end of bellows 24. The metal annulus 30 engages first and second U-shaped metal contacts 32, 34 when the bellows 24 is in an uncollapsed or fully collapsed configuration. When engaging the metal contacts 32, 34, the metal annulus 30 provides a current path between the contacts 32, 34 and switch 22 is closed. When the bellows 24 is partially collapsed maintaining the annulus 30 between the contacts 32, 34, switch 22 is open. Thus, bellows 24, annulus 30 and contacts 32, 34 provide a simple but effective switch mechanism for indicating when the air flow rate through air flow sensor 10 is within the range corresponding to desired slow breathing. The relatively narrow air flow range set by the U-shaped contacts 32, 34 also allows the spirometer electronics to provide a reasonably accurate measure of total inhaled air volume by measuring the time the air flow rate is within the range.

By choosing an appropriate material and wall thickness for bellows 24, the bellows can be made to collapse at any desired air flow rate. For example, a desirable air flow rate for slow deep breathing has been found to be the range of 40 to 60 liters per minute. Other suitable values of air flow rate may be chosen however depending on the patient's characterstics. Experiments have established that for a suitable choice of silicon, bellows wall thickness and orifice size, collapse of the bellows 24 will commence at the desired air flow rate of 40 liters per minute. For example, with a commercially available silicon, grade 595, hardness 40 shore A, and a 0.21 inch diameter orifice and 0.020 inch bellows wall thickness, collapse of the bellows will commence at the desired air flow rate of approximately 40 liters per minute. Other suitable values of air flow rate may be chosen by varying these parameters. This combination of material, wall thickness and orifice size was also found suitable in finding the desired characteristic of approximately linear collapse after the air flow reaches the desired rate. Other materials, wall thickness and orifice diameters, including combinations with more than one orifice, which result in the desired bellows collapse characteristics may be used, however.

In FIG. 3 the spirometer electronics for determining the volume of air inhaled and displaying this information is shown in block diagram form. The spirometer electronics and incentive display are powered by a D.C. power source 15. The supply of power to the spirometer electronics and display is controlled by switch 38 which is in turn opened and closed by air flow sensor 10. As described above, air flow sensor 10 measures the air flow rate therethrough and when the air flow rate is within the desired range closes switch 38. With the air flow rate determined within a relatively narrow range, inhaled air volume may be measured by determining the time during which the air flow rate is within the range. Oscillator 40 provides a source of periodic signals suitable for providing a reference time for determining the period that switch 38 is closed. Oscillator 40 is coupled to a counter 42 which counts the periodic signals supplied by oscillator 40. The output of counter 42 is provided to a decoder 44 which converts the output of counter 42 to a signal suitable for providing to display 46. In one embodiment, the display 46 takes the form of a series of LEDs, and decoder 44 converts the binary output of counter 42 to a signal sequentially activating successive LEDs as the counter output increases.

The preferred embodiment shown in FIG. 3 also includes a hold display 48. The hold display 48, e.g. in the form of a single LED, lights up after the air flow through air flow sensor 10 falls out of the desired range and remains on for a few seconds to encourage the patient to hold the air in his lungs. The power to hold display 48 is maintained by a hold circuit 50 which maintains switch 38 closed for a preselected period of time after the air flow rate falls out of the range set by the air flow sensor 10. The display 46 and decoder 44 are turned off during this period by air flow sensor 10 which is directly coupled along line 52 to the decoder 44.

In FIG. 4 a circuit embodying the operational features shown in FIG. 3 is shown in schematic form. The regulated power source, 15 is provided by a D.C. voltage source in the form of battery 15 in conjunction with a voltage regulator 54. A suitable voltage regulator 54 is a low power 5 volt regulator such as the 78L05 commercially available from several manufacturers. The power source 36 provides D.C. voltage along line 56 to switch 38 and bellows switch mechanism 22. Switch 38 is a semiconductor switch, in the embodiment of FIG. 4 being a PNP bipolar transistor. Other suitable switch devices may be employed, however. Bellows switch mechanism 22 is coupled to the base of transistor switch 38 via inverter 58 (shown implemented as a NAND gate with inputs tied together). When the air flow sensor 10 is not in use, and the bellows 24 is in its uncollapsed state, the conductive annulus 30 engages metal contacts 32, 34 thereby closing bellows switch mechanism 22 and coupling the input of inverter 58 to ground, i.e. at a low logic level. The output of inverter 58 will therefore be at a high logic level maintaining the transistor switch 38 turned off. Thus, when the spirometer is not in use the remainder of the electronics will be without power and will be turned off. A relatively high resistance resistor 60 is provided between the power source 15 and bellows switch mechanism 22 to keep current loss to ground to a minimum thereby preserving the lifetime of battery 15.

When the air flow rate through bellows 24 reaches the desired value, and collapse of bellows 24 commences, bellows switch mechanism 22 will open causing the voltage supplied to the input of inverter 58 to rise to a high level. The output of inverter 58 will thus go low turning on switch 38. With switch 38 turned on, oscillator 40 is activated. In the embodiment shown in FIG. 4, oscillator 40 consists of a commercially available 555 timer 62 connected so as to operate as a multivibrator. The output of the timer/multivibrator 62 is provided along line 64 and will be a square wave signal with the frequency thereof determined by the reciprocal of the resistance R of variable resistor 66 and the capacitance C of capacitor 68, i.e. proportional to 1/RC. Thus, adjusting the variable resistor 66 allows the frequency of the periodic signals provided along line 64 to be preset at a suitable value. The periodic signals are provided along line 64 to the clock input of counter 42, which may be a commercially available binary counter such as the 74161 4 bit counter available from a number of manufacturers. The power and enable inputs of counter 42 are driven directly from the regulated power source 36 along line 70 when switch 38 is closed. Since counter 42 is provided power and enabled upon closing of switch 38, to ensure proper reset a short delay is provided for an enable signal by capacitor 73 and first and second inverters 72, 74 connected between the clear input to counter 42 and the power source 36.

Once switch 38 is closed and counter 42 commences counting the periodic signals from timer/multivibrator 62, the output of counter 42 will be provided as a binary value to decoder 44. In the embodiment shown in FIG. 4, counter 42 outputs a 4 bit binary signal to decoder 44 which may be any suitable decoder such as the 74154 decoder available from several manufacturers. The enable/disable inputs of decoder 44 are coupled along line 78 to the output of inverter 58. Therefore when bellows switch 22 is open, line 78 coupled to the output of inverter 58 will be low and decoder 44 is enabled. Decoder 44 converts the 4 bit binary signal from counter 42 to a signal on 1 of 16 output lines coupled to a corresponding number of light emitting diodes 76. This series of LEDs 76 forms the incentive display 46. Thus, once switch 38 is closed by the partial collapse of bellows 24, LEDs 76 will sequentially light corresponding to the successive binary output of counter 42 and therefore to inhaled air volume.

When the collapse of bellows 24 either exceeds the upper range set by contacts 32, 34 or falls back to the uncollapsed state, bellows switch 22 will again close, causing the output of inverter 58 to go high. This will provide a high logic level on line 78 to the enable/disable input of decoder 44, turning off decoder 44 and LEDs 76. Switch 38 is maintained closed, however, due to the action of hold circuit 50 which maintains the base drive of switch 38 at a low level for a preselected period of time. The delay function of delay circuit 50 is accomplished by a timer 80 which may be a commercially available 555 timer. The trigger and threshold inputs of timer 80 are connected to capacitor 82 and resistor 84 along line 83. The capacitance of capacitor 82 and resistance of resistor 84 determine the time delay from the input to inverter 86 going from low to high to the output of timer 80 along line 88 going from low to high. With a suitable choice of resistor 84 and capacitor 82, the delay may be set at two seconds corresponding to a suitable period of breath retention by the patient. Diode 90 and a resistor 92 of relatively small resistance are provided to allow switch 38 to rapidly turn on without a significant delay. The hold display 48 is provided by a single LED 94 in conjunction with flip-flop 96, such as the commercially available 7474 J-type flip-flop. LED 94 is turned on by the combination of the clock input to flip-flop 96 going high in conjunction with the clear and preset inputs being held high by switch 38 remaining closed by the action of hold circuit 50. After the delay period elapses, switch 38 turns off, turning off the power to the hold display 48 and turning off the hold display LED 94. The circuit shown in FIG. 4 thus provides an effective and inexpensive implementation of the desired functions of the spirometer electronics. It should be understood that the specific circuit system described is only exemplary and it is within the broad scope of the invention to employ other circuit systems to perform the timing and related functions. For example, in mass production, a single custom integrated circuit may be used to perform all or a substantive part of the functions of the circuit system.

While the present invention has been described in terms of a preferred embodiment of the spirometer electronics having specific circuit elements and commercially available circuit parts, it will be appreciated that wide variations will be possible while implementing the basic timing and display functions. Also, the basic external configuration of the incentive spirometer may be changed from that shown in FIG. 1 and varying forms of incentive display and hold incentive display may be employed. Furthermore, the design of the bellows switch mechanism may be varied while maintaining the desired response characteristics to air flow rate. It will be apparent to one skilled in the art that other changes in the details of the preferred embodiment described above may be made and such alternate embodiments are within the scope of the present invention. Thus, the present invention is not intended to be limited to the above-described preferred embodiment and is instead best described by the following claims.

I claim:

1. An incentive spirometer for use by a patient during breathing exercises comprising:
    an air flow rate sensor having a mouthpiece and an air flow rate switch coupled to said mouthpiece, said switch having flexible means, which flexes in response to changes in air pressure caused by changes in air flow rate, for activating said switch when the air flow rate through said sensor is within a preselected relatively narrow range corresponding to a desired breathing rate for said patient and for deactivating said switch when the air flow rate through said sensor is not within said range;
    timing means coupled to said air flow rate switch for determining the time that said air flow rate switch is activated and providing an output corresponding to said time; and
    display means coupled to said timing means for providing a display corresponding to the output of said timing means.

2. An incentive spirometer as set out in claim 1 wherein said timing means comprises a digital timer including an oscillator and digital counter.

3. An incentive spirometer as set out in claim 1 further comprising means for automatically activating said timing means and said display means in response to the activation of said air flow rate switch and wherein said timing means and said display means are in a low power consumption standby mode until such activation.

4. An incentive spirometer as set out in claim 1 further comprising means for deactivating said display means when said air flow rate, as determined by said air flow rate sensor, falls out of said preselected range between breaths and for thereby preventing continuous provision of said display during repeated short, shallow breaths.

5. An incentive spirometer as set out in claim 1 wherein said predetermined range of air flow rate is an air flow rate between 40 liters per minute and 60 liters per minute.

6. An incentive spirometer for use by a patient during breathing exercises, comprising:
    an air flow sensor having;
        a mouthpiece,
        a collapsible bellows coupled to said mouthpiece, the end of said bellows opposite said mouthpiece having one or more calculated size orifices therein to allow air flow through said bellows, said bellows being of configuration and material such that partial collapse of said bellows will occur when a change of pressure occurs within said bellows as a result of change in the rate of air flow through said bellows, and
        means responsive to the position of said bellows for determining when the bellows collapse configuration falls within a predetermined range of partial collapse corresponding to a rate of air flow through said bellows determined to be suitable for remedial breathing by the patient;
    timing means coupled to said air flow sensor for measuring the time that said bellows is partially collapsed within said predetermined range and providing an electrical output signal corresponding to said measured time; and
    display means coupled to said timing means for providing display varying with the output signal provided by said timing means.

7. An incentive spirometer as set out in claim 6 further comprising hold display means coupled to said air flow sensor for providing a display for a predetermined time after said bellows falls out of said predetermined range of partial collapse as incentive for breath retention.

8. An incentive spirometer as set out in claim 6 wherein said display means comprises a series of light emitting diodes sequentially lighting as the output of said timing means varies with increasing measured time.

9. An incentive spirometer as set out in claim 6 wherein said timing means comprises a source of periodic signals, a counter coupled to said source of periodic signals, and a decoder coupled to said counter and said display means.

10. An incentive spirometer as set out in claim 6 wherein said means responsive to the position of the bellows comprises first and second electrical contacts positioned adjacent said bellows and a third electrical contact coupled to said bellows so as to engage said first and second contacts when said bellows configuration falls outside said predetermined range of partial collapse.

11. An incentive spirometer as set out in claim 6 wherein said rate of air flow is an air flow rate greater than 40 liters per minute.

12. An incentive spirometer comprising:
    a mouthpiece;
    an air flow rate sensor attached to the mouthpiece including air flow rate switch means for determining when the rate of air flow therethrough falls within a predetermined range determined as suitable for remedial breathing exercises, having first and second electrical contacts and flexible means for selectively electrically decoupling said first and second contacts in response to variations in air pressure corresponding to said air flow rate being within said predetermined range and for selectively electrically coupling said first and second contacts when said air flow rate is not within said predetermined range;
    oscillator means for providing periodic signals;
    counter means responsive to said air flow rate switch means for counting said periodic signals when said air flow rate falls within said predetermined range and providing an output corresponding to the number of signals counted; and
    display means coupled to said counter means for providing a display varying with said count output.

13. An incentive spirometer as set out in claim 12 further comprising hold display means responsive to said air flow rate switch means for providing a hold display for a predetermined period of time after said air flow rate falls below said predetermined range.

14. An incentive spirometer as set out in claim 12 wherein said flexible means comprises a bellows having a preselected collapse profile in response to air flow therethrough such that bellows collapse commences at an air flow rate corresponding to the beginning of said predetermined air flow range and a conductive member coupled to said bellows so as to selectively engage and electrically couple said first and second contacts.

15. An incentive spirometer as set out in claim 12 wherein said predetermined range of air flow rate is an air flow rate between 40 liters per minute and 60 liters per minute.

16. An incentive spirometer for use during breathing exercises, comprising:
    a mouthpiece;
    air flow sensor means attached to the mouthpiece for determining when the rate of air flow therethrough is in a predetermined range chosen as suitable for breathing exercises, including a collapsible bellows of preselected resilience and configuration such that said bellows is responsive to changes in air pressure caused by changes in air flow rate therethrough and such that said bellows is in a partially collapsed configuration when the rate of air flow therethrough falls within said predetermined range and said bellows is not in said partially collapsed configuration when the rate of air flow therethrough does not fall within said predetermined range;
    a power source;
    oscillator means for outputting periodic signals;
    semiconductor switch means coupled to said air flow sensor means for coupling said power source to said oscillator means when said air flow rate is in said predetermined range;
    counter means coupled to said oscillator means for providing an output corresponding to the number of signals received from said oscillator means; and
    display means coupled to said counter means for providing a visual display varying with the output of said counter means.

17. An incentive spirometer as set out in claim 16 further comprising hold display means for providing a hold display for a predetermined period of time after said air flow rate falls below said predetermined range and wherein said counter means includes decoder means for providing a sequentially varying output related to the number of signals received from said oscillator means and said decoder means is coupled to said air flow sensor means and is enabled when said air flow rate is within said range and disabled when said air flow rate is outside said range.

18. An incentive spirometer as set out in claim 16 wherein said predetermined range of air flow rate is an air flow rate greater than 40 liters per minute.

19. A device for providing reinforcing feedback during remedial breathing exercises, comprising:
 an air flow sensor having a mouthpiece, a collapsible bellows coupled to said mouthpiece, the end of said bellows opposite said mouthpiece having one or more orifices therein of predetermined size and an outer annulus of conductive material attached to the circumference thereof, and a hollow enclosure having two openings positioned at opposite ends of said enclosure, one opening adjustably receiving said mouthpiece, said enclosure further having first and second conductive elements positioned on opposite interior walls of said enclosure so as to engage said conductive annulus when said bellows is in predetermined configurations and so as to be disengaged from said conductive annulus when said bellows is not in said predetermined configurations;
 a power source;
 a switch coupled to said power source and said air flow sensor such that said switch is closed and allows current flow therethrough from said power source when said bellows is partially collapsed such that said annulus does not engage said conductive elements;
 an oscillator selectively coupled to said power source by said switch for providing periodic signals when said switch is closed;
 a counter coupled to said oscillator and receiving said periodic signals therefrom for providing a varying output related to the number of periodic signals received from said oscillator; and
 a display coupled to said counter for providing a visual display related to the counter output.

20. A device as set out in claim 19 further comprising a hold circuit having an inverter and a delay timer coupled to said switch to maintain said switch closed for a predetermined time after said annulus reengages said conductive elements and a hold display activated when said annulus reengages said conductive elements and deactivated when said switch is opened.

21. A device as set out in claim 19 wherein said counter is a binary counter providing an output in binary form and further comprising a decoder coupled to said display and said counter and outputting a sequential output corresponding to said binary counter output.

22. A device as set out in claim 19 wherein said bellows is composed of silicon of grade 595 and hardness 40 shore A, and the walls thereof are approximately 0.020 inches thick, and has a single orifice approximately 0.21 inches in diameter.

* * * * *